(12) United States Patent
Pringle et al.

(10) Patent No.: US 8,904,664 B2
(45) Date of Patent: Dec. 9, 2014

(54) DEHYDRATION DEVICE AND METHODS FOR DRYING BIOLOGICAL MATERIALS

(71) Applicant: MiMedx Group, Inc., Marietta, GA (US)

(72) Inventors: Douglas Pringle, Marietta, GA (US); Michael Lepeak, Marietta, GA (US)

(73) Assignee: MiMedx Group, Inc., Marietta, GA (US)

(*) Notice: Subject to any disclaimer, the term of this patent is extended or adjusted under 35 U.S.C. 154(b) by 0 days.

(21) Appl. No.: 13/744,332

(22) Filed: Jan. 17, 2013

(65) Prior Publication Data

US 2014/0051059 A1    Feb. 20, 2014

Related U.S. Application Data

(60) Provisional application No. 61/683,700, filed on Aug. 15, 2012.

(51) Int. Cl.
| | |
|---|---|
| *F26B 3/06* | (2006.01) |
| *A01N 1/02* | (2006.01) |
| *A61K 35/50* | (2006.01) |
| *A61L 31/00* | (2006.01) |
| *A61L 26/00* | (2006.01) |
| *A61K 45/06* | (2006.01) |
| *A61K 9/14* | (2006.01) |
| *A61L 29/00* | (2006.01) |
| *A61L 27/36* | (2006.01) |

(52) U.S. Cl.
CPC .............. *A61K 35/50* (2013.01); *A01N 1/0284* (2013.01); *A61L 31/005* (2013.01); *A61L 26/0057* (2013.01); *A61K 45/06* (2013.01); *A61K 9/14* (2013.01); *A61L 29/005* (2013.01); *A61L 27/36* (2013.01)
USPC ............ 34/105; 424/484; 623/23.72; 435/1.2

(58) Field of Classification Search
CPC ................ F26B 3/00; F26B 3/02; F26B 3/04; F26B 3/06; F26B 5/00; F26B 7/00; F26B 9/00; F26B 9/06; F26B 9/10; F26B 9/103; F26B 11/00; F26B 11/0445; F26B 19/00; A61F 2/02; A61F 2/08
USPC ..................... 34/90, 104, 201, 210, 218, 242; 424/400, 422, 484; 623/23.72, 14.13, 623/13.17; 435/1.1, 1.2
See application file for complete search history.

(56) References Cited

U.S. PATENT DOCUMENTS

| | | | |
|---|---|---|---|
| 2,694,914 A | 11/1954 | Glover, Jr. | |
| 3,885,320 A * | 5/1975 | Hodson et al. | ............. 34/287 |

(Continued)

FOREIGN PATENT DOCUMENTS

| | | |
|---|---|---|
| CN | 101433556 | 5/2009 |
| EP | 0 431 164 | 6/1991 |

(Continued)

OTHER PUBLICATIONS

MiMedx drying google search conducted on Apr. 8, 2014.*

(Continued)

*Primary Examiner* — Steve M Gravini
(74) *Attorney, Agent, or Firm* — Foley & Lardner LLP

(57) ABSTRACT

This invention relates generally to a dehydration device and methods for drying biological materials to produce dried biological materials having enhanced structural properties. More specifically, the invention relates to a dehydration device and related methods for drying biological tissue to produce enhanced tissue grafts.

8 Claims, 4 Drawing Sheets

(56) References Cited

U.S. PATENT DOCUMENTS

| | | | |
|---|---|---|---|
| 4,564,368 A | | 1/1986 | Sawyer et al. |
| 4,745,771 A | | 5/1988 | Linner et al. |
| 4,807,442 A | * | 2/1989 | Linner et al. ............... 62/55.5 |
| 4,865,871 A | * | 9/1989 | Livesey et al. ............... 435/1.3 |
| 4,964,280 A | * | 10/1990 | Piunno et al. ............... 62/78 |
| 4,968,325 A | | 11/1990 | Black et al. |
| 5,118,867 A | | 6/1992 | Bahrmann et al. |
| 5,284,655 A | | 2/1994 | Bogdansky et al. |
| 5,780,295 A | * | 7/1998 | Livesey et al. ............ 435/307.1 |
| 6,030,635 A | | 2/2000 | Gertzman et al. |
| 6,163,979 A | * | 12/2000 | Oetjen et al. ............... 34/286 |
| 6,387,369 B1 | | 5/2002 | Pittenger et al. |
| 6,652,583 B2 | * | 11/2003 | Hopkins et al. ............ 623/2.13 |
| 7,311,904 B2 | | 12/2007 | Hariri |
| 7,311,905 B2 | | 12/2007 | Hariri |
| 8,067,044 B2 | | 11/2011 | Henry et al. |
| 8,153,162 B2 | | 4/2012 | Tseng et al. |
| 8,196,416 B2 | * | 6/2012 | Uri et al. ............... 62/63 |
| 8,323,701 B2 | | 12/2012 | Daniel et al. |
| 8,357,403 B2 | | 1/2013 | Daniel et al. |
| 8,372,439 B2 | | 2/2013 | Daniel et al. |
| 2002/0123141 A1 | | 9/2002 | Hariri |
| 2002/0160510 A1 | | 10/2002 | Hariri |
| 2003/0032179 A1 | | 2/2003 | Hariri |
| 2003/0187515 A1 | | 10/2003 | Hariri et al. |
| 2004/0048796 A1 | | 3/2004 | Hariri et al. |
| 2006/0140913 A1 | | 6/2006 | Bhatia |
| 2006/0210532 A1 | | 9/2006 | Carmeliet et al. |
| 2007/0021762 A1 | | 1/2007 | Liu et al. |
| 2007/0144062 A1 | * | 6/2007 | Wright ............... 44/589 |
| 2007/0202189 A1 | | 8/2007 | Ahlfors |
| 2007/0248575 A1 | | 10/2007 | Connor et al. |
| 2007/0299043 A1 | | 12/2007 | Hunter et al. |
| 2008/0046095 A1 | | 2/2008 | Daniel |
| 2008/0050347 A1 | | 2/2008 | Ichim |
| 2008/0069895 A1 | | 3/2008 | Liu et al. |
| 2008/0131966 A1 | | 6/2008 | Hariri |
| 2008/0181967 A1 | | 7/2008 | Liu et al. |
| 2008/0233552 A1 | | 9/2008 | Ma et al. |
| 2009/0012629 A1 | | 1/2009 | Yao et al. |
| 2009/0036996 A1 | | 2/2009 | Roeber |
| 2009/0056162 A1 | * | 3/2009 | McMahon et al. ............... 34/511 |
| 2009/0142831 A1 | | 6/2009 | Hariri |
| 2009/0291891 A1 | | 11/2009 | Neufeld |
| 2010/0028849 A1 | | 2/2010 | Shelby et al. |
| 2010/0104539 A1 | | 4/2010 | Daniel et al. |
| 2010/0136114 A1 | | 6/2010 | Mao |
| 2010/0143312 A1 | | 6/2010 | Hariri et al. |
| 2010/0178297 A1 | | 7/2010 | Carmeliet et al. |
| 2010/0199514 A1 | * | 8/2010 | Camisa ............... 34/201 |
| 2010/0209408 A1 | | 8/2010 | Stephen et al. |
| 2010/0260847 A1 | | 10/2010 | Hariri |
| 2010/0272782 A1 | | 10/2010 | Owens et al. |
| 2011/0044997 A1 | | 2/2011 | Rankin et al. |
| 2011/0177150 A1 | | 7/2011 | Pathak et al. |
| 2011/0206776 A1 | | 8/2011 | Tom et al. |
| 2011/0307059 A1 | | 12/2011 | Young et al. |
| 2012/0010708 A1 | | 1/2012 | Young et al. |
| 2012/0030963 A1 | | 2/2012 | Durance et al. |
| 2012/0078378 A1 | | 3/2012 | Daniel et al. |
| 2013/0230561 A1 | | 9/2013 | Daniel et al. |

FOREIGN PATENT DOCUMENTS

| | | |
|---|---|---|
| EP | 0431479 A1 | 6/1991 |
| KR | 10/1991/0011272 | 8/1991 |
| KR | 10/1991/0011727 | 8/1991 |
| KR | 2001/100588 | 11/2001 |
| WO | WO-01/08716 A1 | 2/2001 |
| WO | WO-2005/017165 | 2/2005 |
| WO | WO-2009/033160 | 3/2009 |
| WO | WO-2009/048908 | 4/2009 |
| WO | WO-2009/132186 A1 | 10/2009 |
| WO | WO-2010/029344 | 3/2010 |
| WO | WO-2012/112410 | 8/2012 |
| WO | WO-2012/112417 A2 | 8/2012 |
| WO | WO-2012/112441 A1 | 8/2012 |

OTHER PUBLICATIONS

U.S. Appl. No. 13/647,308, filed Oct. 8, 2012, Daniel et al.
U.S. Appl. No. 13/719,148, filed Feb. 13, 2012, Morse et al.
U.S. Appl. No. 13/744,331, filed Jan. 17, 2013, Koob et al.
U.S. Appl. No. 13/745,642, filed Jan. 18, 2013, Koob et al.
U.S. Appl. No. 13/787,612, filed Mar. 6, 2013, Morse et al.
U.S. Appl. No. 13/815,747, filed Mar. 15, 2013, Daniel et al.
U.S. Appl. No. 13/815,784, filed Mar. 15, 2013, Koob et al.
U.S. Appl. No. 13/815,873, filed Mar. 15, 2013, Brown et al.
U.S. Appl. No. 13/963,984, filed Aug. 9, 2013, Daniel et al.
U.S. Appl. No. 13/967,326, filed Aug. 14, 2013, Koob et al.
U.S. Appl. No. 13/983,301, filed Feb. 13, 2012, Morse et al.
U.S. Appl. No. 14/050,218, filed Oct. 9, 2013, Brown et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Produce Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+stem cells from bone-marrow microenvironment," Nat. Med., (2002), 8(8):841-849.
International Preliminary Report on Patentability for copending PCT Application No. PCT/US2012/024798, dated Feb. 1, 2013.
International Search Report and Written Opinion for copending PCT Application No. PCT/US2013/054322, dated Oct. 22, 2013.
International Search Report for copending PCT Application No. PCT/US2012/024798, dated Jun. 20, 2012.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Mayfield et al., "Watertight closure of spinal dura mater: Technical note," J. Neurosurg., (1975), 43(5):639-640.
U.S. Appl. No. 61/683,697, filed Aug. 15, 2012, Daniel.
U.S. Appl. No. 61/683,699, filed Aug. 15, 2012.
U.S. Appl. No. 61/683,700, filed Aug. 15, 2012, Daniel.
U.S. Appl. No. 13/688,091, filed Nov. 28, 2012, Spencer et al.
U.S. Appl. No. 13/815,753, filed Mar. 15, 2013, Koob et al.
PCT International Search Report and Written Opinion for copending PCT Application No. PCT/US2013/054319, dated Nov. 13, 2013.
PCT International Search Report and Written Opinion for copending PCT Application No. PCT/US2013/055003, dated Nov. 19, 2013.
PCT International Search Report and Written Opinion for copending PCT Application No. PCT/US2013/054320, dated Nov. 6, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054325, dated Oct. 28, 2013.
Tao, et al., "Implantation of amniotic membrane to reduce postlaminectomy epidurla adhesions," Eur. Spine. J., (2009), 18:1202-1212.
http://proxybiomedical.com/Images/ML005-01-Rev002.pdf (accessed on Jun. 5, 2014).
International Search Report and Written Opinion for PCT/US2014/012141, dated May 20, 2014.
Koob et al., "Biological properties of dehydrated human amnion-chorion composite graft: implications for chronic wound healing", International Wound Healing, 2013, 10(5):493-500.
MiMedx Press Release, "MiMedx Scientific Study is Electronically Published in the International Wound Journal", 2013.
Nagaya et al., "Transplantation of mesenchymal stem cells improves cardiac function in a rat model of dilated cardiomyopathy", Circulation, 2005, 112(8):1128-1135.

(56) References Cited

OTHER PUBLICATIONS

Parolini et al., "Toward cell therapy using placenta-derived cells: disease mechanisms, cell biology, preclinical studies, and regulatory aspects at the round table", Stem Cells and Development, 2010, 19(2):143-154.

PCT International Preliminary Report on Patentability dated Jan. 16, 2014 in related PCT Patent Application No. PCT/US12/66862.
PCT International Search Report and Written Opinion dated Jan. 9, 2014 in related PCT Patent Application No. PCT/US2013/064146.

* cited by examiner

DEHYDRATION DEVICE AND METHODS FOR DRYING BIOLOGICAL MATERIALS

CROSS-REFERENCE TO RELATED APPLICATIONS

This application claims priority under 35 U.S.C. §119(e) to U.S. Provisional Application Ser. No. 61/683,700, filed Aug. 15, 2012, which application is incorporated herein by reference in its entirety.

BACKGROUND OF THE INVENTION

1. Field of the Invention

This invention relates generally to a dehydration device and methods for drying biological materials to produce dried biological materials having enhanced structural properties. More specifically, the invention relates to a dehydration device and related methods for drying biological tissue to produce enhanced tissue grafts.

2. State of the Art

The storage and preservation of biological materials is crucial for the success of many applications involving biological materials. Drying, dessication and dehydration (hereinafter used interchangeably) is one of the tools and methods available. To date, a variety of devices and methods have been used to prepare biological materials in a dehydrated form in order to confer benefits such as reduced weight and reduced storage space, and also increased chemical and/or structural stability. While each of these devices have certain benefits, they also come with certain detriments including one or more of the following, prolonged drying time, limited capacity, uneven drying, and the like.

Current drying technologies employ, for example, air drying, drying with microwaves, drying at sublimation phase, and drying at various temperature conditions. These methods, however, can take an extended period of time to complete and/or may lack uniformity as to the drying process and rate. Other methods involve lyophilization and/or freeze-drying, which may allow for extended storage of some dried biological materials but are unsuitable for others. Further, some of these methods use chemicals such as dimethyl sulfoxide (DMSO), carbohydrates, paraformaldehyde and the like to fix biological materials during the lyophilization process. These chemicals often modify the biological materials and compromise their functions. Some other methods use sugars to stabilize biological materials prior to freeze-drying. These types of processes, however, may produce ice crystals and damage biological material structures.

Accordingly, there is a need in the art for a dehydration device and methods of using the device that enhance the rate and uniformity of the dehydration process without causing damage to their structure or function.

SUMMARY OF THE INVENTION

This invention is directed, in part, to a dehydration device that provides enhanced rates and/or uniformity of dehydration for drying biological materials. In various embodiments, the dehydration device is configured such that it is capable of drying multiple samples at a time thereby enhancing the overall efficiency of dehydration.

One exemplary embodiment of this invention is directed to a dehydration device for use in drying biological material, comprising: a drying housing defining a drying chamber and defining inflow and outflow apertures; an inflow plenum in communication with the inflow apertures; an outflow plenum in communication with the outflow apertures; and an air-moving assembly configured to deliver air to the inflow plenum and receive the return air from the outflow plenum; wherein in use the biological material is placed into the drying chamber to dehydrate the biological material.

In another embodiment of the invention, the inflow and outflow plenums are integrally formed with the drying housing and the inflow and outflow apertures are provided by arrays of uniformly arranged and aligned apertures.

In yet another embodiment of the invention, the dehydration device further comprises an air-heating assembly configured to selectively heat the air delivered to the inflow plenum. In another embodiment, the dehydration device further comprises a control system configured to control the operating parameters of the device to dry the biological material.

In other embodiments of the invention, the drying chamber is maintained at a humidity of less than 10%. In an additional embodiment, the air delivered by the air-moving assembly is an inert gas. Further, in other embodiments, two or more biological materials may be placed into the drying chamber to be dehydrated at the same time.

In another exemplary embodiment of the invention, the biological material is placental tissue. As such, another embodiment of the invention is directed to a dehydration device for use in drying placental tissue, comprising: a drying housing defining a drying chamber and defining inflow and outflow apertures; an inflow plenum in communication with the inflow apertures; an outflow plenum in communication with the outflow apertures; an air-moving assembly configured to deliver air to the inflow plenum and receive the return air from the outflow plenum; an air-heating assembly configured to selectively heat the air delivered to the inflow plenum; and a control system configured to control the operating parameters of the device to dry the placental tissue, wherein in use the placental tissue is placed into the drying chamber and the control system is operated to deliver heated air to the drying chamber to dehydrate the placental tissue.

Other aspects of the invention are found throughout the specification.

BRIEF DESCRIPTION OF THE DRAWINGS

The accompanying drawings, which are incorporated in and constitute a part of this specification, illustrate several aspects described below.

DETAILED DESCRIPTION

Figure 1:
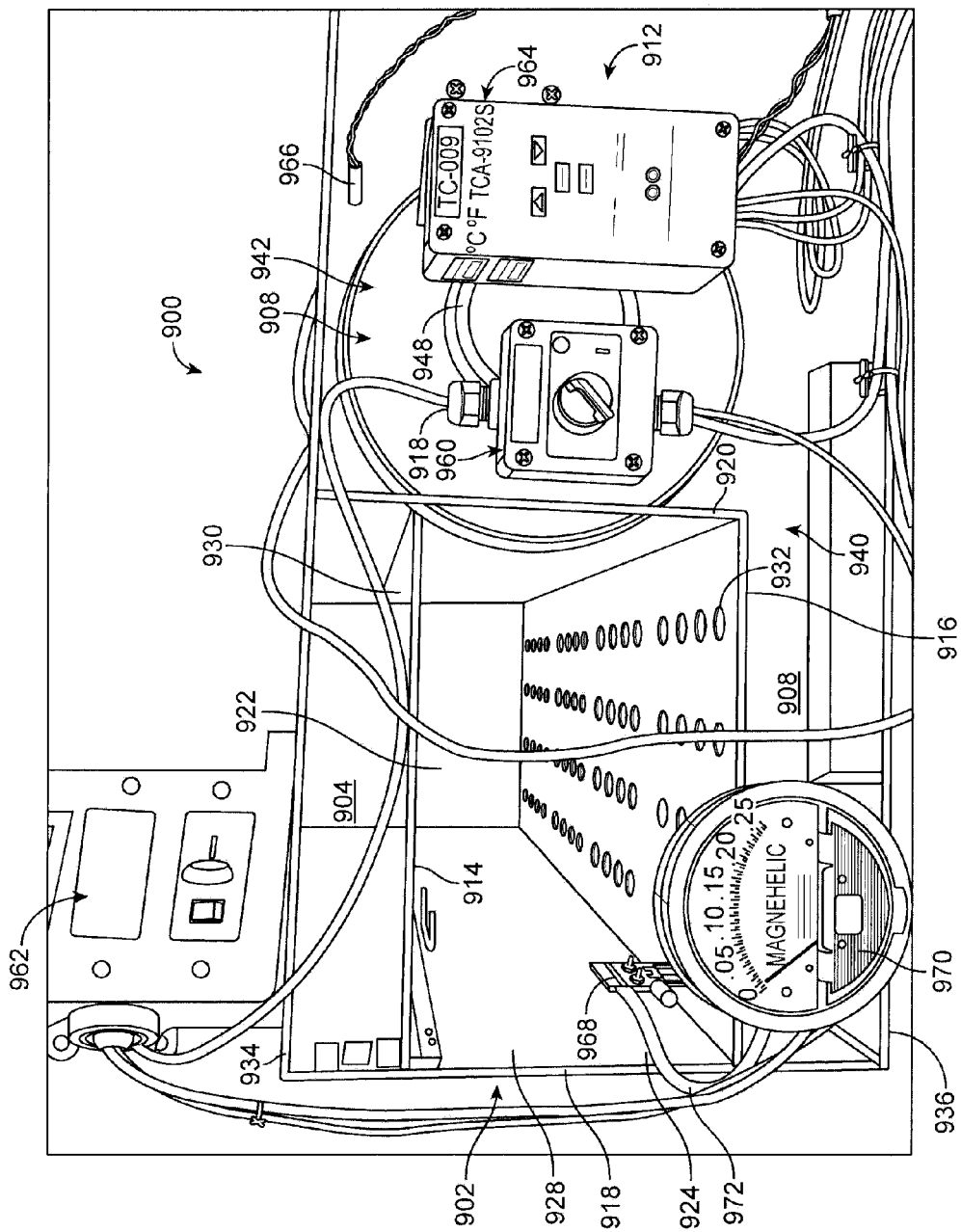
FIG. 1 shows a forward perspective view of a dehydration device as described herein.

This invention relates generally to a dehydration device and methods for drying biological materials to produce dried biological materials having enhanced structural properties. More specifically, the invention relates to a dehydration device and related methods for drying biological tissue to produce enhanced tissue grafts.

Before the present invention is disclosed and described, it is to be understood that the aspects described below are not limited to specific devices, methods or uses thereof as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise.

The term "subject" as used herein is any vertebrate organism including but not limited to mammalian subjects such as humans, farm animals, domesticated pets and the like.

The term "biological material(s)" refers to any material obtained from a biological source, including cells, tissues, organs, and/or organisms, and any combination thereof. This term refers both to eukaryotic and prokaryotic cells from either plant or animal source, present, for example, in a cell culture; to tissues (from plant or animal) present in a tissue culture, to isolated organs, to tissues present inside the organism, as well as to the full organism itself (both full plant and full animal organism).

The term "placental tissue" refers to any and all of the well known components of the placenta including but not limited to amnion, chorion, Wharton's Jelly, and the like. In one preferred embodiment, the placental tissue does not include any of the umbilical cord components (e.g., Wharton's jelly, umbilical cord vein and artery, and surrounding membrane).

Titles or subtitles may be used in the specification for the convenience of a reader, which are not intended to influence the scope of the present invention. Additionally, some terms used in this specification are more specifically defined herein.

The invention is described more fully hereinafter with reference to the accompanying figures, in which exemplary embodiments of the invention are shown. This invention may, however, be embodied in many different forms and should not be construed as limited to the exemplary embodiments set forth herein.

Dehydration Device

For the purposes of the disclosure set forth below, the biological material as exemplified with reference to the figures herein is placental tissue for the preparation of enhanced placental tissue grafts. However, it should be understood that any biological material can be dehydrated using the dehydration device as described herein. As such, in various aspects of the invention, it is understood that the optimal conditions for the dehydration process are dependant on the particular biological material or materials intended to be dried. As such, it should be understood that different biological materials will benefit from different dehydration conditions. It is further contemplated that more than one biological material can be dehydrated at the same time. Accordingly, the suitable conditions for drying any particular biological material can be determined by one of skill in the art when using the dehydration device disclosed herein to enhance the rate and uniformity of the drying process.

In one aspect of the invention, placental tissue can be dehydrated to form a placental tissue graft using an innovative dehydration device as described herein. Use of the dehydration device enhances the rate and uniformity of the dehydration process. In one embodiment, the drying time can be accelerated by up to 40% in one configuration of the dehydration device in comparison to conventional drying ovens. In certain aspects, the placental tissue graft is placed onto a drying fixture described herein and the drying fixture with tissue graft is inserted into the dehydration device for performing the dehydration process. In other aspects, multiple placental tissue grafts can be placed onto the drying fixture to dry more than one placental tissue grafts in the dehydration device at the same time. Although the dehydration device is useful in dehydrating the tissue grafts described herein, they can be used for dehydrating objects other than placental tissue.

FIGS. 1-4 show an innovative dehydration device 900 according to an example embodiment that is well-suited for use in the herein-described dehydration processes. The dehydration device 900 includes a drying housing 902, and inflow plenum 904, and outflow plenum 906, an air-moving assembly 908, an air-heating assembly 910, and a control system 912.

In exemplary embodiments, the drying housing 902 defines a drying chamber into which the placental tissue is placed for drying during the dehydration process (e.g., onto a drying fixture). In typical embodiments, the drying housing 902 (and thus the drying chamber it defines) is formed by six generally planar walls arranged together in a generally rectanguloid shape. In other embodiments, the drying housing 902, and/or the drying chamber it defines, has a different regular or irregular shape such as spherical or ellipsoidal.

Figure 2:
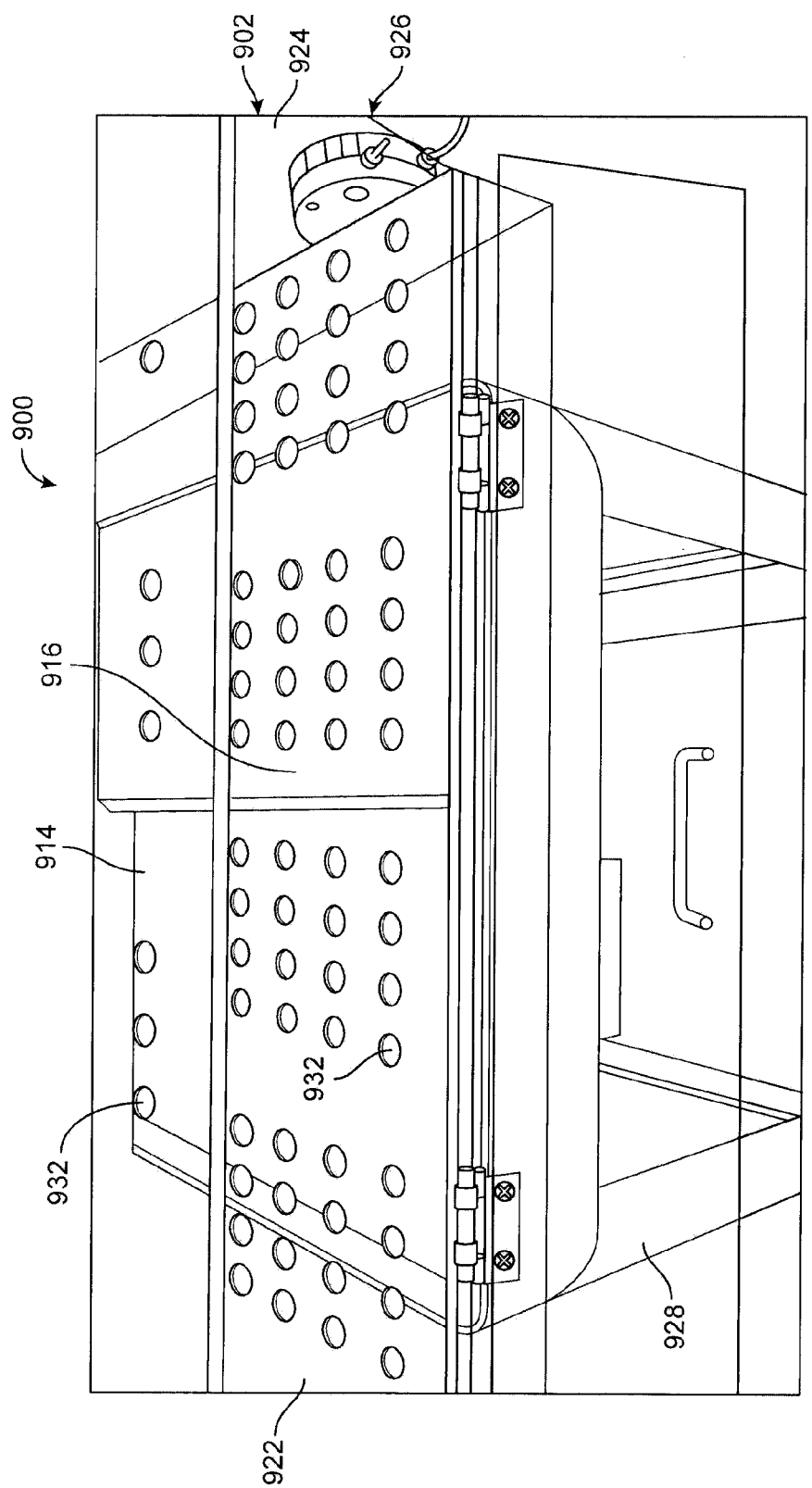
FIG. 2 shows an overhead perspective view of a dehydration device as described herein.
Figure 3:
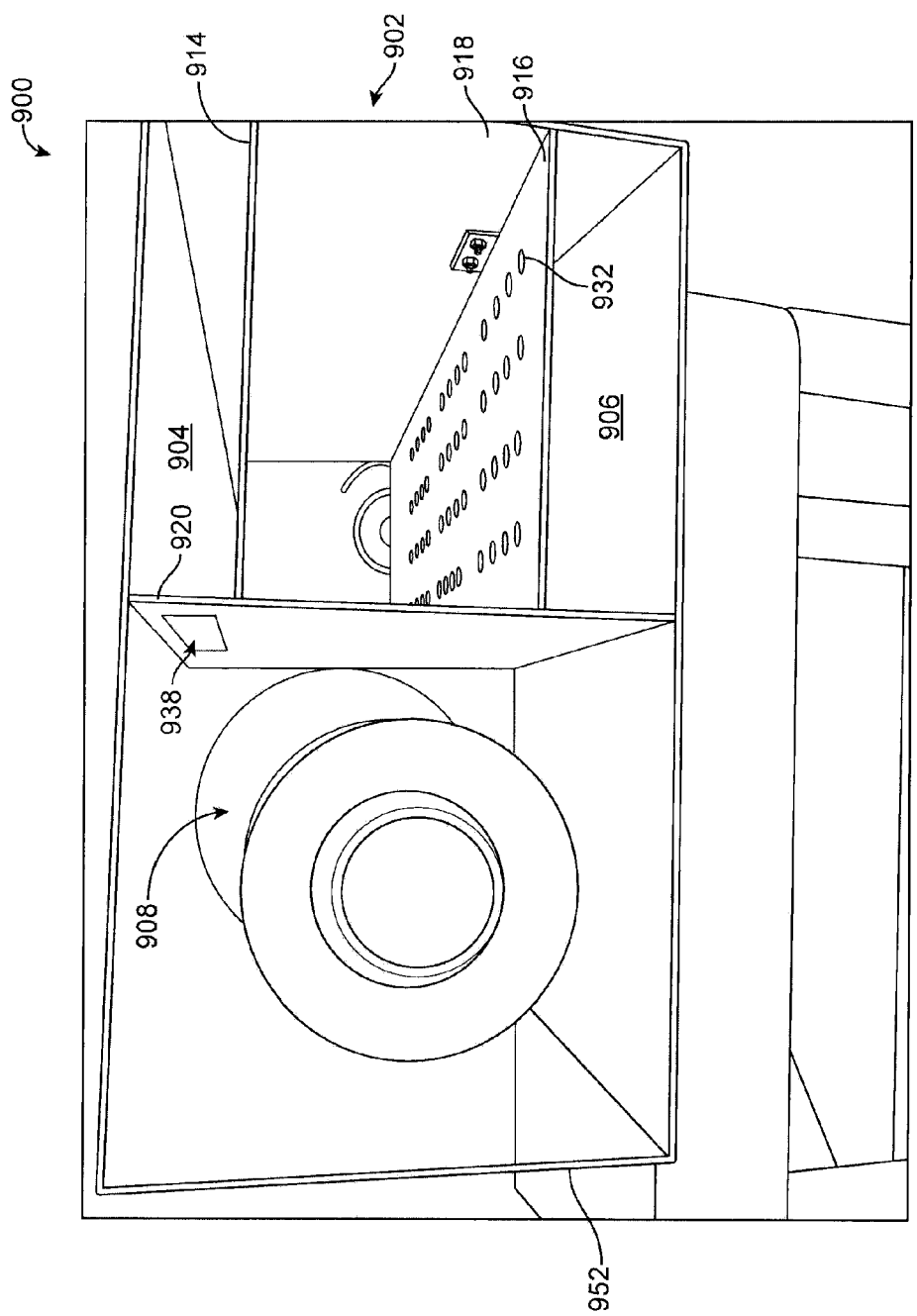
FIG. 3 shows a side perspective view of a dehydration device as described herein.
Figure 4:
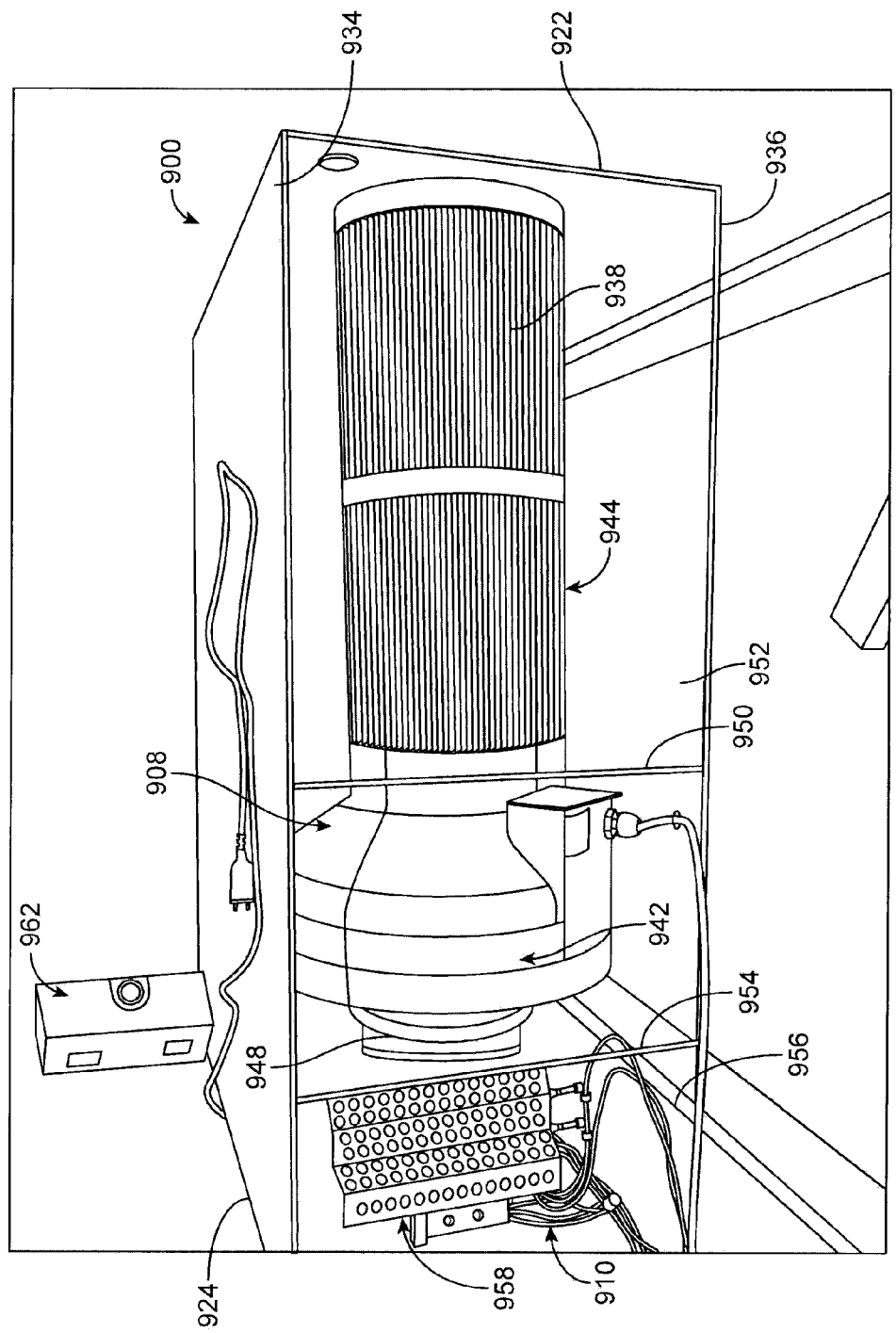
FIG. 4 shows a back perspective view of a dehydration device as described herein.

In the depicted embodiment, the drying housing 902 is formed by top and bottom opposing walls 914 and 916, first and second opposing sidewalls 918 and 920, and first and second opposing endwalls 922 and 924. The drying housing 902 includes a doorway opening 926 and a door 928 (e.g. hingedly coupled to the housing and including a pull-knob) in at least one of the walls (e.g., sidewall 918) for inserting the placental tissue on a fixture for dehydration and then removing the dried tissue. (FIG. 1 shows the door 928 in a closed position and FIG. 2 shows it in an opened position.) The walls of the housing 902 are typically made of a material selected for rigidity, strength, and heat-resistance, for example a thermoplastic polycarbonate material, such as LEXAN® (General Electric), or other suitable materials, including but not limited to, acrylic (e.g., PLEXIGLAS), glass, ceramic, or other polymeric materials.

In some embodiments, at least two of the walls of the housing 902 each define at least one respective aperture through which air can flow. In the depicted embodiment, for example, the top and bottom opposing walls 914 and 916 have an array of inflow and outflow apertures 930 and 932, respectively, formed in them. In such embodiments, the placental tissue graft is placed into the drying chamber (e.g., on a fixture) supported by the bottom wall 916 and typically at least partially covering at least one of the outflow apertures 932. The size, shape, and position of the apertures 930 and 932 are selected based on the range of operating parameters (volumetric flow rate, flow pattern, temperature, pressure, time/duration, etc. of the air flowing through the housing 902) of the device 900 as may be desired for drying the placental tissue. Thus, the apertures 930 and 932 can be circular, aligned with corresponding apertures in the opposing wall, arranged in segmented rows and/or columns, and arranged uniformly (for a generally uniform temperature and drying effect across the chamber), as depicted. In other embodiments, the apertures have a non-circular shape (e.g., polygonal or elliptical), have differing sizes (e.g., interspersed larger and smaller apertures, or differing inflow and outflow aperture sizes), and/or are formed in an irregular and/or non-aligning pattern. And in yet other embodiments, the apertures are formed in only one of the walls, more than two of the walls, or the opposing sidewalls 918 and 920 (instead of or in addition to the opposing top and bottom walls 914 and 916), and/or the inflow plenum 904 can be eliminated and piping coupled between the air-moving assembly 908 and an inflow one of the walls (e.g., top wall 914).

The inflow plenum 904 and the outflow plenum 906 are positioned in communication with the inflow apertures 930 and the outflow apertures 932, respectively. The plenums 904 and 906 help generate an even distribution of the pressure, flow, and temperature of the air flowing through the drying housing 902. In the depicted embodiment, the inflow plenum 904 is formed by first vertically upward extensions of the opposing sidewalls 918 and 920 and the opposing endwalls 922 and 924 together with the housing top wall 914 and an opposing inflow-plenum top wall 934. And the outflow plenum 906 is formed by second vertically downward extensions of the opposing sidewalls 918 and 920 and the opposing endwalls 922 and 924 together with the housing bottom wall 916 and an opposing outflow-plenum bottom wall 936. In other embodiments, the plenums 904 and 906 are eliminated and the air-moving assembly 908 is piped directly to the drying housing 902.

The inflow plenum 904 and the outflow plenum 906 include at least one inflow port 938 and outflow port 940, respectively. In the depicted embodiment, the inflow port 938 is defined by a generally rectangular opening formed in the sidewall 920 at an upper portion thereof and at a first/distal portion thereof, and the outflow port 940 is defined by a generally rectangular gap in the same sidewall (i.e., an absence of the second extension of the wall) but at a lower portion thereof and at a second/proximal portion thereof. In this way, the air flows laterally into the inflow plenum 904 at the first/distal and upper portion of the dehydration device 900 and then distributes proximally within the inflow plenum. Then the air flows down through the inflow apertures 930, down through and across the drying chamber, down through the outflow apertures 932, down into the outflow plenum 906, and laterally out at the second/proximal and lower portion of the device 900. The plenums 904 and 906 provide for generally evenly distributed airflow across the tissue even though the air enters the inflow plenum at the first/distal portion of the dehydration device 900 and exits the outflow plenum at the second/proximal portion (while flowing from top to bottom through the drying chamber). Alternatively, the inflow and outflow ports 938 and 940 can be positioned to provide airflow from bottom to top and/or from side to side through the drying chamber, and/or they can have other regular or irregular shapes such as circular. In other embodiments, the direction of air flow and where it flows within the drying chamber may be from perpendicular to, at an acute angle to, substantially parallel or otherwise relative to the placental tissue. In certain aspects, airflow provided through the drying chamber at a particular angle of deflection may enhance the rate of dehydration. A suitable angle of deflection can be determined by one of skill in the art depending on the rate of dehydration desired.

The air-moving assembly 908 can be of a commercially available type for use in sterile/clean-air environments such as medical laboratories. Typically, the air-moving assembly 908 includes a blower 942 and a filter 944. The blower 942 can be of a conventional type, for example including an electric motor and a fan enclosed within a housing. In some embodiments, the blower 942 is capable of providing an air flow rate through the drying chamber at a flow velocity rate of between 130 ft/m to 200 ft/m. And the filter 944 can be of a conventional type, for example a cylindrical HEPA air filter with an internal bore. Typically, such filter 944 mounts to and extends from the blower 942, and air flows axially through the internal bore and radially outward through the filter media. In this regard, the filter 944 prevents contamination of air in both closed or open loop airflow systems. As such, use of the filter 944 provides a biohazard protection feature and also safeguards the room air integrity by preventing cross-contamination if more than one dehydration device is in use. In this regard, multiple dehydration devices can be placed in close proximity without the risk of cross-contamination. This provides several advantages from a production perspective for scaling up, as more than one dehydration devices can be stacked on top of each other in order in close proximity.

In other aspects, the dehydration device 900 can be configured in an open loop (to provide fresh intake air) or in a closed airflow loop (to re-circulate the air). In exemplary embodiments, the dehydration device 900 is configured in an open airflow loop. In one aspect, the open loop provides a gradual exchange of air by introducing a portion of fresh air into the drying chamber when the dehydration device 900 is in use. In this aspect, fresh air is introduced into the drying chamber to reduce the relative humidity within the drying chamber. In certain aspects, fresh air is introduced into the drying chamber in a suitable amount such that 3 to 15% of the total volume of air in the drying chamber is fresh air. In other aspects, the amount of fresh air that is introduced into the drying chamber is from 5 to 10% fresh air. When using an open loop system, the relative humidity within the drying chamber can be monitored, as well as the humidity of the room in which the dehydration device is located, to ensure optimal drying conditions.

In closed-loop designs, an air outlet surface 946 of the filter 944 is in sealed communication with the inflow port 938 of the inflow plenum 904, and an air intake 948 of the blower 942 is in sealed communication with the outflow port 940 of the outflow plenum 906. In the depicted embodiment, for example, the air outlet surface 946 of the filter 944 is enclosed in a first/distal delivery chamber formed by lateral extensions of the plenum top and bottom walls 934 and 936, a lateral extension of the first/distal endwall 922 and an opposing second/proximal delivery-chamber endwall 950, and the second sidewall 920 and an opposing delivery-chamber sidewall 952. And the air intake 948 of the blower 942 is sealed in communication with a second/proximal return chamber formed by lateral extensions of the plenum top and bottom walls 934 and 936, a lateral extension of the second/proximal endwall 924 and an opposing first/distal return-chamber endwall 954 (having an return opening in sealed communication with the blower air intake), and the second sidewall 920 and an opposing return-chamber sidewall 956. A sidewall section can be provided to enclose the blower 942 or this can be left out to allow ambient air exposure to prevent the blower from overheating. In the depicted embodiments, the result is that the outer walls of the dehydration device 900 form a rectanguloid structure. In other embodiments, the air outlet surface 946 of the filter 944 is piped to the inflow port 938 of the inflow plenum 904 and the air intake 948 of the blower 942 is piped to the outflow port 940 of the outflow plenum 906.

In other embodiments, the air-heating assembly 910 includes at least one heating element 958, which can be of a conventional type such as a commercially available electric-resistance heating element. The heating element 958 is typically positioned adjacent the air intake 948 of the blower 942, for example mounted on a bracket within the return chamber, as depicted.

The control system 912 includes conventional controls for controlling the operating parameters (airflow rate, pressure, temperature, time/duration, humidity, etc.) of the dehydration device 900. Such conventional controls typically include a main power switch 960 that is wired to provide power to a variable resistance device 962 and a control unit 964. The main power switch 960 is wired to a power source such as conventional 120/240 line voltage. The variable resistance device 962 (e.g., a silicon controlled rectifier or SCR) is wired (for power and control) to the heating element 958 (e.g., via the control unit 964) for temperature control. At least one heat sensor 966 is positioned in the return chamber and wired to the control unit 964 to provide an input for use in temperature control. And the control unit 964 is wired (for power and control) to the blower 942 for controlling the volume flow rate (and thus also the pressure) and the time/duration of the dehydration cycle. In addition, typical embodiments such as that depicted include a pressure sensor 968 in (or at least exposed to) the drying chamber, a pressure gauge display 970 (e.g., mounted to the drying housing 902), and a fluid connection 972 (e.g., tubing) interconnecting the two parts. In other embodiments, a humidity sensor (not shown) is positioned in the chamber to monitor the humidity in the return chamber.

In exemplary embodiments, room air is delivered into the drying chamber. In one aspect, room air is drawn from air contained in a clean room. In other aspects, an inert gas can be delivered into the drying chamber to further enhance the dehydration process. Non-limiting examples of suitable inert gas include nitrogen and argon gases, or any suitable gas known by those of ordinary skill in the art. In other aspects, the ambient atmosphere provided in the drying chamber during depositing and/or drying of the biological material has a low humidity. In these aspects, providing a low humidity in the drying chamber further enhances the rate and/or uniformity of the dehydration process. In this regard, the term "low humidity" is herein meant to refer to a relative humidity of less than 30%, in some aspects to less than 20% humidity, in further aspects to less than 10% humidity and in even further aspects to less than 5% humidity. In further exemplary embodiments of the invention, the humidity, pressure and/or temperature differentials may be established before, during or after the biological material to be dehydrated is introduced into the drying chamber. Additionally, one or more differentials can be maintained while the product is being dehydrated.

Enhanced Biological Materials

It is contemplated that drying biological material, such as placental tissue, with a dehydration device according to the invention provides a biological material with superior structural properties, due to the enhanced rate and uniformity of the drying process. In certain aspects, it is contemplated that a placental tissue graft prepared by drying placental tissue in the dehydration device according to the invention will possess superior structural properties including but not limited to improved tissue graft integrity, tensile and shear strength and controlled water content throughout the tissue graft.

In particular aspects, the invention minimizes the disadvantages associated with conventional drying techniques, such as a non-uniform water content in a tissue graft when preparing tissue grafts from placental tissue. For example, tissue grafts tend to accumulate tissue fluid in cyst-like pockets between adjacent layers after application due to a lack of uniformity in water content throughout the graft. Fluid pockets are detrimental to wound healing because they retard connective tissue ingrowth, provide an environment conducive to bacterial growth and prevent the apposition of natural body tissues which promotes healing and tensile strength.

Drying a placental tissue in the dehydration device according to the invention overcomes these disadvantages by allowing for controlled dehydration in both the rate of dehydration and the uniformity of dehydration, which confers advantages to the structural properties of prepared tissue grafts, such as improved tissue graft integrity, tensile and shear strength and controlled water content. In one aspect, a tissue graft dried according to the invention has been found to enhance the overall adhesion of the placental tissue layers to one another in both adhesive strength and uniformity. It is believed that this enhanced adhesion promotes contact of the tissue graft with endogeneous fluids and cells (by increasing the surface area of the implanted graft). In another aspect, the tissue grafts prepared according to the invention possess enhanced tensile and shear strength throughout the entirety of the tissue graft due to the uniformity of drying.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Tissue Grafts with Micronized Placental Tissue

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

A detailed description of suitable cross-linking agents and procedures is provided in concurrently filed U.S. patent application Ser. No. 61/683,697 filed as attorney docket number 102741-0250 and entitled PLACENTAL TISSUE GRAFTS MODIFIED WITH A CROSS-LINKING AGENT AND METHODS OF MAKING AND USING THE SAME which application is incorporated herein by reference in its entirety.

A detailed description of reinforced placental tissue grafts is provided in concurrently filed U.S. patent application Ser. No. 61/683,699 filed as and entitled REINFORCED PLACENTAL TISSUE GRAFTS AND METHODS OF MAKING AND USING THE SAME which application is incorporated herein by reference in its entirety.

A detailed description of making and using micronized placental tissue and extracts thereof is provided in concurrently filed U.S. patent application Ser. No. 61/683,700 filed as attorney docket number 102741-0400 and entitled MICRONIZED PLACENTAL TISSUE COMPOSITIONS AND METHODS OF MAKING AND USING THE SAME which application is incorporated herein by reference in its entirety.

Example 2

Preparation of Dehydrated Placental Tissue

A placental tissue was prepared according to the methods set forth in Example 1 and placed in a dehydration device located in a clean room. Inflow apertures located on the top wall of the drying housing were spaced 1.5 inches apart from left to right and 2.25 inches apart from front to back, each aperture having a diameter of 0.625 inches. Outflow apertures located on the bottom wall of the drying housing were spaced 1.5 inches apart from left to right and 2.31 inches from front to back, each aperture having a diameter of 0.75 inches.

Room air was circulated through the dehydration device using a Fantech FR150 6 inch duct fan (manufactured by Fantech Inc., Lenexa, Kans.) and filtered by a system of HEPA filters to deliver air to the placental tissue. A Heatrex 276 350 W heater (manufactured by Heatrex, Inc., Meadville, Pa.) attached proximal to the air intake of the fan was operated to heat the air to a temperature of about 45° C. The temperature during the dehydrating process was monitored with a temperature controller (model: TCA-9102S, manufactured by Control Products, Inc., Chanhassen, Minn.) positioned in the return chamber. Additionally, the humidity level was monitored with a humidity sensor (model: HS-50-S, manufactured by Control Products, Inc., Chanhassen, Minn.) with a target desired humidity range of about 20% relative humidity. Negative pressure in the drying chamber was provided at about 0.03 in. W.C. and monitored throughout the dehydration process with a pressure gauge (model: 2000-00, manufactured by Dwyer Instruments, Inc., Michigan City, Ind.). Air flow was provided through the drying chamber at a flow velocity rate of about 150 ft/m and was monitored by the central control system. A programmable logic controller (PLC) (model: Allan-Bradley Micro830, manufactured by Rockwell Automation, Inc., Milwaukee, Wis.) was used for the automation of all processes described.

The placental tissue was dehydrated under the stated conditions for about 4.5 hours, after which the dehydrated placental tissue was allowed to rest in the dehydration chamber.

In the foregoing description, various features are grouped together in a single embodiment for the purpose of streamlining the disclosure. This method of disclosure is not to be interpreted as reflecting an intention that the claimed embodiments of the invention require more features than are expressly recited in the claim. Rather, inventive subject matter lies in less than all features of a single disclosed embodiment.

The disclosure set forth above is provided to give those of ordinary skill in the art a complete disclosure and description of how to make and use embodiments of the device and methods of the present invention, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference in their entirety as if each such publication, patent or patent application were specifically and individually indicated to be incorporated herein by reference.

What is claimed:

1. A dehydration device for use in drying placental tissue, comprising:
    a drying housing defining a drying chamber and defining inflow and outflow apertures;
    an inflow plenum in communication with the inflow apertures;
    an outflow plenum in communication with the outflow apertures; and
    an air-moving assembly configured to deliver air to the inflow plenum and receive the return air from the outflow plenum;
    wherein in use the placental tissue is placed into the drying chamber to dehydrate the placental tissue.

2. The dehydration device of claim 1, wherein the inflow and outflow plenums are integrally formed with the drying housing and the inflow and outflow apertures are provided by arrays of uniformly arranged and aligned apertures.

3. The dehydration device of claim 1, further comprising an air-heating assembly configured to selectively heat the air delivered to the inflow plenum.

4. The dehydration device of claim 1, further comprising a control system configured to control the operating parameters of the device to dry the biological material.

5. The dehydration device of claim 1, wherein the drying chamber is maintained at a humidity of less than 10%.

6. The dehydration device of claim 1, wherein the air delivered by the air-moving assembly is an inert gas.

7. The dehydration device of claim 1, wherein two or more biological materials are placed into the drying chamber to be dehydrated at the same time.

8. A dehydration device for use in drying placental tissue, comprising:
    a drying housing defining a drying chamber and defining inflow and outflow apertures;
    an inflow plenum in communication with the inflow apertures;
    an outflow plenum in communication with the outflow apertures;
    an air-moving assembly configured to deliver air to the inflow plenum and receive the return air from the outflow plenum;
    an air-heating assembly configured to selectively heat the air delivered to the inflow plenum; and
    a control system configured to control the operating parameters of the device to dry the placental tissue,
    wherein in use the placental tissue is placed into the drying chamber and the control system is operated to deliver heated air to the drying chamber to dehydrate the placental tissue.

* * * * *